United States Patent
Baets

(10) Patent No.: US 9,689,007 B2
(45) Date of Patent: Jun. 27, 2017

(54) PROCESS FOR THE FERMENTATIVE PRODUCTION OF LACTIC ACID FROM A PLANT EXTRACT THE PRESENCE OF A CAUSTIC MAGNESIUM SALT

(71) Applicant: PURAC BIOCHEM BV, Gorinchem (NL)

(72) Inventor: Peter Johannes Marie Baets, Spijk (NL)

(73) Assignee: PURAC BIOCHEM B.V., Gorinchem (NL)

(*) Notice: Subject to any disclaimer, the term of this patent is extended or adjusted under 35 U.S.C. 154(b) by 62 days.

(21) Appl. No.: 14/365,818

(22) PCT Filed: Dec. 14, 2012

(86) PCT No.: PCT/EP2012/075659
§ 371 (c)(1),
(2) Date: Jun. 16, 2014

(87) PCT Pub. No.: WO2013/087901
PCT Pub. Date: Jun. 20, 2013

(65) Prior Publication Data
US 2015/0118722 A1    Apr. 30, 2015

Related U.S. Application Data

(60) Provisional application No. 61/576,374, filed on Dec. 16, 2011.

(30) Foreign Application Priority Data

Dec. 16, 2011 (EP) ..................................... 11194094

(51) Int. Cl.
C12P 9/00 (2006.01)
C12P 7/56 (2006.01)

(52) U.S. Cl.
CPC .. *C12P 7/56* (2013.01); *C12P 9/00* (2013.01)

(58) Field of Classification Search
None
See application file for complete search history.

(56) References Cited

U.S. PATENT DOCUMENTS 3,429,777 A     2/1969 Bode
2010/0112652 A1 5/2010 Bogaert et al.

FOREIGN PATENT DOCUMENTS

| EP | 2 239 333 A1 | 10/2010 |
|----|--------------|---------|
| WO | WO 00/17378 A2 | 3/2000 |
| WO | WO 03/095659 A1 | 11/2003 |
| WO | WO 2005/123647 A1 | 12/2005 |
| WO | WO 2006/001034 A2 | 1/2006 |
| WO | WO 2011/095631 A1 | 8/2011 |

OTHER PUBLICATIONS

GEA, Evaporators for Stillage Concentration, Document created Aug. 29, 2012, Available Online at: www.gea.com/global/en/binaries/ GEA_Evaporators-For-Stillage-Concentration_brochure_EN_tcm11-22947.pdf.*
Lee et al., Production of Lactic Acid from Paper Sludge by Simultaneous Saccharification and Fermentation, Adv Biochem Engin/Biotechnol (2004) 87: 173-194.*
Kosugi et al., "Ethanol and Lactic Acid Production Using Sap Squeezed from Old Oil Palm Trunks Felled for Replanting," *Journal of Bioscience and Bioengineering*, 2010, vol. 110, No. 3, pp. 322-325.
Lee et al., "Hydrolysis of Paper Sludge Using Mixed Cellulase System: Enzymatic Hydrolysis of Paper Sludge," *American Chemical Society*, 2002, pp. 121-138.
Jemai et al., "Pulsed Electric Field Assisted Pressing of Sugar Beet Slices: Towards a Novel Process of Cold Juice Extraction," *Biosystems Engineering*, 2006, vol. 93, No. 1, pp. 57-68.
International Search Report issued in International Patent Application No. PCT/EP2012/075659 mailed Jan. 31, 2013.
International Preliminary Report on Patentability issued in International Patent Application No. PCT/EP2012/075659 mailed Jun. 17, 2014.

* cited by examiner

*Primary Examiner* — Karen Cochrane Carlson
*Assistant Examiner* — Jennifer M. H. Tichy
(74) *Attorney, Agent, or Firm* — Oliff PLC

(57) ABSTRACT

A method is described for producing lactate or lactic acid from a plant extract, such as oil palm frond extract, via fermentation. In particular, the method includes providing a fermentation medium that includes at least 25 wt. % of a plant extract containing fermentable carbohydrates, fermenting the fermentation medium by means of a lactic acid producing microorganism in the presence of a caustic magnesium salt to provide a fermentation broth containing at the most 9.5 wt. % magnesium lactate at the end of fermentation, the magnesium lactate being in soluble form during and at the end of fermentation; and recovering lactate or lactic acid from the magnesium lactate containing fermentation broth.

21 Claims, No Drawings

PROCESS FOR THE FERMENTATIVE PRODUCTION OF LACTIC ACID FROM A PLANT EXTRACT THE PRESENCE OF A CAUSTIC MAGNESIUM SALT

The present invention relates to the production of lactic acid via fermentation.

Lactic acid may be used in numerous applications such as the preservation of food and the preparation of biodegradable polymers. In some of these applications the quality of the starting lactic acid is of utmost importance. For instance, in the production of lactide and polylactic acid it is desirable to start with a lactic acid with high stereochemical purity. Further, the presence of impurities in the starting lactic acid may result in undesirable racemisation of lactic acid moieties leading to a lactide and a polylactic acid product of lower quality.

The increasing demands for high quality products together with the need to achieve production costs compatible with the commodities market, make it essential to be able to reduce the costs of the starting materials for the production of lactic acid while at the same time not compromising the quality.

Lactic acid is often manufactured via fermentation of carbohydrates by microorganisms. Despite the longstanding practice to produce lactic acid via fermentation, one of the challenges in the manufacture of lactic acid is still to obtain the acid in a relatively pure form while at the same time carrying out the process in an economical manner on a scale which is commercially attractive.

Common carbohydrate sources used in said fermentation processes include purified beet sugar, cane sugar, starches and starch derivatives such as refined glucose syrups originating from the hydrolysis of starch, which starches may be maize starch, tapioca starch, wheat starch, potato starch, and the like. In order to reduce production costs of lactic acid produced by fermentation, using an inexpensive carbohydrate source is desirable. For instance, unrefined sources of fermentable carbohydrates may be used. Such unrefined sources may be unrefined plant extracts or intermediates or by-products from the agricultural industry such as starch syrup, molasses, whey, cane derivatives such as raw cane juice and hydrolyzed bagasse).

Generally, soluble and insoluble impurities are present in substantial amounts in unrefined plant extracts. Such impurities may cause problems in the production of lactic acid, e.g. they may inhibit the growth of the lactic acid producing microorganisms or they may render it difficult to recover the final lactic acid product. This is particularly problematic for plant extracts with a relatively low content of fermentable carbohydrates. In such plant extracts, the concentration of impurities (and in particular salts of, for instance, sodium, potassium and calcium cations) relative to the concentration of fermentable sugar is relatively high when compared to, for instance, plant extracts with higher concentrations of fermentable carbohydrates. Generally, fermentation broths obtained from low-sugar plant extracts also have a higher concentration of impurities relative to the lactic acid product, implicating the necessity for extensive purification of lactic acid. These drawbacks make plant extracts with a relatively low content of fermentable carbohydrates poor carbohydrate sources for lactic acid production via fermentation. However, given the availability of raw materials, which in many occasions would simply be discarded, there is an interest to use such plant extracts.

US 2010/0112652 describes a process for producing lactic acid by fermentation of a sugarcane extract by means of microorganisms belonging to the *Bacillus* or *Sporolactobacillus* genus, whereby the fermentation medium is self-sufficient. During fermentation, calcium hydroxide is added to maintain the pH of the fermentation medium.

Kosugi et al. (*J. Bioscience and Bioengineering*, 2010 vol. 110, p. 322) describe ethanol and lactic acid production via fermentation using sap squeezed from old oil palm trunks felled for replanting. In this document, a 5-fold dilution of a juice (to obtain a final sugar concentration of 16.7 g/L and obtained from the inner part of oil palm trunks) is fermented to provide lactic acid. The production of lactic acid in the fermentation medium is monitored by high-performance anion-exchange chromatography. This document does not address the recovery of the lactic acid from the fermentation broth.

U.S. Pat. No. 3,429,777 describes a process for the production of magnesium lactate from crude, highly impure lactic acid solutions contaminated with soluble proteins and soluble phosphates, wherein magnesium hydroxide is added to the fermentation broth after ending the fermentation.

EP 2 239 333 relates to processes for the recovery of components from bio-organic juice streams using ion exchange. The bio-organic juice is usually an aqueous solution comprising components derived from plants, animals and/or microorganisms. In the examples lactic acid is recovered from fermented grass juice with a weak anion ion exchange resin. The recovery of lactic acid from the fermented juice with an anion exchange resin is a costly and complex process if applied on an industrial scale. A particular disadvantage of using ion exchangers is the need for costly regeneration cycles which generate waste by-products.

The instant invention provides a method for producing lactate or lactic acid via fermentation of a lactic acid producing microorganism, comprising the use of a fermentation medium comprising a plant extract as a source of fermentable carbohydrates, the plant extract being present in the fermentation medium in a concentration of at least 25 wt. %, and the addition of a caustic magnesium salt during fermentation to produce a fermentation broth containing magnesium lactate, wherein the fermentation conditions are such that the magnesium lactate concentration in the fermentation broth at the end of fermentation is at most 9.5 wt. % and no precipitation of magnesium lactate in the fermentation broth, during fermentation or when the fermentation has ended, occurs or has occurred. Such a fermentation advantageously allows purification of the fermentation broth by a method comprising firstly separating solid material, including biomass, from the fermentation broth, and then crystallizing magnesium lactate from the clear broth.

The magnesium lactate concentration in the fermentation broth at the end of fermentation typically may be measured at the temperature at which the fermentation was performed, as is described herein below. The value of at the most 9.5 wt. % is obtained when measuring at a temperature of 80° C.

To achieve a magnesium lactate concentration in the fermentation broth at the end of fermentation which is at most 9.5 wt. %, the fermentation medium comprising the plant extract preferably contains fermentable carbohydrates in a concentration of at most 9.5 wt. %. When the fermentation medium contains fermentable carbohydrates in a higher concentration than 9.5 wt. %, the caustic magnesium salt may be added in a suitably diluted form, to ensure that the magnesium lactate concentration in the fermentation broth at the end of fermentation is at most 9.5 wt. %. The lower limit for the amount of fermentable carbohydrates generally is determined by economic considerations and may be 0.5 wt. %.

The plant extract which is used in the fermentation medium has a liquid phase, and the liquid phase of the plant extract contains a low amount of fermentable carbohydrates, preferably an amount of 0.5-9.5 wt. % fermentable carbohydrates.

It has now been found that the use of a caustic magnesium salt as a neutralization agent in the fermentation of such "low-sugar" plant extracts advantageously makes these low-sugar plant extracts viable carbohydrate sources for the production of lactic acid. In particular, the method as described herein allows obtaining lactic acid in good yield and purity, in particular a good stereochemical purity. Further, the method as described herein allows keeping to a minimum any purification, concentration or dilution steps of the low-sugar plant extract, thereby minimizing sugar loss. All in all, the method as described herein is particularly suitable for producing lactic acid on an industrial scale. These and other advantages of using a low-sugar plant extract as carbohydrate source for lactic acid production via fermentation with a caustic magnesium salt will become evident from the following more detailed description of the invention.

In principle, the plant extract for use in the method as described herein may be derived from any plant material, originating from cultivated plants (crop plants), from wild plants, as well as from mixtures of plants.

Of particular interest are plant materials or plant extracts which are available in abundance. For example, plant-derived by-products or waste streams of the agricultural industry (e.g. oil palm fronds) or of any other industry concerned with the processing of plant materials (e.g. potato waste, paper sludge, corn cob residue, bread waste) may be of interest.

The term "plant extract" as used herein refers to a material which is obtained from plants and/or plant parts by physical means (e.g. by comminuting, pressing, heating, pulsed electric field assisted treatments, shear treatments and pressure wave treatments), by chemical means (e.g. by treatment with an acid, a base, a solvent) and/or by biochemical means (e.g. by treatment with hydrolytic enzymes, microorganisms).

The plant extract may in principle be obtained from a whole plant and/or any plant part, e.g. leafs, stems, flowers, fruits, seeds, peels, roots. Generally, the content of fermentable carbohydrates of extracts from, for instance, leafs and stems may be lower than that of other parts of the plant, such as fruits. However, any part of the plant may be used.

An example is an extract from oil palm fronds. Oil palms are tropical palm trees of species such as *Elaeis guineensis* and *Elaeis oleifera* which are used in the production of oil. Oil is extracted from both the pulp of the fruit (palm oil) and the kernel (palm kernel oil, used in foods and for soap manufacture). Palm oil is widely used for industrial purposes and is the most produced plant oil. During the harvest of oil palm fruits the compound leafs of oil palm trees are cut to reach the fruit bunches that contain the palm oil. Said compound leafs are commonly referred to as oil palm fronds (OPFs) and each blade is divided in what is known as leaflets. After the harvest of oil palm fruits the oil palm fronds are normally left in the plantation field, where they are naturally degraded under tropical conditions. In 2009, 83 million tons of palm fronds were available in Malaysia. In one embodiment, a plant extract as described herein advantageously is an extract from oil palm fronds (OPF extract). The leaflets of oil palm fronds may be removed prior to obtaining the OPF extract. For instance, an OPF pulp or an OPF juice may be obtained from whole oil palm fronds or from leaflet free oil palm fronds.

Other examples of suitable plant extracts include, for instance, plant extracts obtained from crops such as forage grasses, corn, rice, alfalfa, wheat, clover, spinach, soy, leguminous plants, grains, beets, peas, beans, potatoes, carrots, rape, cassava, sweet potato, sugarcane, algae, soy, fibre crops such as flax and hemp, vegetables, vegetable waste and others.

Streams obtained from industrially processed parts of plants, including waste streams resulting from such processes (e.g. potato waste, paper sludge, corn cob residue, bread waste) may also be used as plant extract. A particular example of such a plant extract is a paper sludge hydrolysate obtained by hydrolysing paper sludge with cellulolytic enzymes. See for instance the article "Hydrolysis of Paper Sludge Using Mixed Cellulase System: Enzymatic Hydrolysis of Paper Sludge" by Sang-Mok Lee et al., in chapter 10 (pages 121-138) of the book Biological systems Engineering of 2002, which describes the preparation of a paper sludge hydrolysate.

The plant extract has a liquid phase and may optionally have a solid phase. In particular, the plant extract may be in liquid form or in semisolid form. For instance, the plant extract may be a pulp (semisolid) or a juice (liquid). The plant juice may be a clear juice or may comprise solid particles, like the solid particles suspended in a cloudy juice.

Suitable plant extracts are plant extracts having a low content of fermentable carbohydrates, i.e. from 0.5 to 9.5 wt. % of fermentable carbohydrates in the liquid phase of the plant extract. In particular, the amount of fermentable carbohydrates in the liquid phase of the plant extract may range from 2 to 9.5 wt. % or from 3 to 9.5 wt. %. Alternatively, the amount of fermentable carbohydrates in the liquid phase of the plant extract may range from 1 to 8 wt. %, more in particular from 2 to 5 wt. %.

Plant extracts that are suitable for use in the method as described herein do not necessarily need to be subjected to extensive processing steps, such as concentration and/or purification, prior to being used, and may be used as such in the fermentation medium.

The term "fermentable carbohydrates" as used herein refers to carbohydrates which can be fermented by a lactic acid producing microorganism. Generally, fermentable carbohydrates are C5 sugars, C6 sugars, oligomers thereof (e.g. dimeric C12 sugars) and/or polymers thereof. By C5 sugars and C6 sugars is meant saccharides with 5 and 6 carbon atoms, respectively, and by C12 sugars it is meant saccharides with 12 carbon atoms (e.g. a disaccharide). The type of fermentable carbohydrates that a specific microorganism is able to ferment may vary and typically depends on the lactic acid-producing microorganism used. Examples of common sugars fermentable by lactic acid producing microorganisms may include C5 sugars such as arabinose, xylose and ribose; C6 sugars such as glucose, fructose, galactose, rhamnose and mannose; and C12 sugars such as sucrose, maltose and isomaltose. The type of sugar that a specific microorganism is able to ferment is commonly known to the skilled person.

The amount of fermentable carbohydrates may be measured by high-pH anion exchange chromatography. A sample of the plant extract is filtered to separate the liquid phase from any solid particles and a chromatogram of the liquid phase is obtained, e.g. with a pulsed amperometric detector (HPAEC-PAD). The carbohydrate composition of the liquid phase may then be determined based on a calibration performed by using appropriate standards (e.g. C5, C6 and/or C12 sugar standards).

In the method as described herein, the plant extract may be produced by processing plant materials as described herein. The plant extract may also be obtained from a commercial supplier.

Processing plant materials may be done with at least one of a physical treatment, a chemical treatment and a biochemical treatment, as described hereinabove.

Physical treatments by comminuting may comprise, for instance, cutting, shredding and/or mincing plant materials to provide, for instance, plant pieces, a plant particulate or a plant pulp. Alternatively or additionally, physical treatments may comprise pressing the plant materials as such or pressing the plant pieces, plant particulate or plant pulp to provide a plant juice. Pressing the plant materials may be performed by, for instance, using a sugar-cane press or a juicer.

A pulsed electric field assisted process or press may also be used. Pulsed electric field assisted processing advantageously reduces losses of sugar in the plant residue, by enhancing extraction of sugar. Reference is made to the publication of A. B. Jemai in Biosystems Engineering (2006) 93(1), 57-68, describing pulsed electric field assisted pressing of sugar beet slices.

Chemical treatments and biochemical treatments may also be used to increase the amount of dimeric and/or monomeric fermentable carbohydrates in the liquid phase of the extract. For instance, polysaccharides (e.g. starch, cellulose or hemicellulose) may be enzymatically hydrolyzed to dimeric or monomeric saccharides.

Processing of the plant materials may be performed at the site where the plant materials are collected, e.g. at the plantation fields. Such processing may be performed with mobile units (e.g. a portable press) or in small processing plants located at the fields.

Processing the materials at the collecting site may advantageously facilitate the transport, e.g., to a processing plant. Comminuted materials may generally be of easier transportation than whole plant materials. Also by processing the plant materials at the collecting site plant residues may be left behind. This advantageously reduces the volume of materials to be transported and may contribute to reducing the environmental impact of harvesting plant materials. For instance, by leaving plant residues at the collecting site the residues may still contribute to the nutritional value of the soil whilst by extracting fermentable carbohydrates from the plant materials the emission of greenhouse gases may be diminished. Further, by leaving the pressed plant materials at the plantation fields no additional disposal channels need to be provided for the plant residues.

In one embodiment, oil palm fronds which, for instance, are cut during the harvest of oil palm fruits may be processed at the plantation fields to provide an OPF extract. This advantageously allows, for instance, for the oil palm fronds to be pressed when freshly cut. Freshly cut oil palm fronds are generally easier to press and have a minimum microbial contamination.

The plant extract may be subjected to a preservation step and/or sterilization step to eliminate and/or to prevent the presence of microorganisms (such as yeast, fungi and bacteria) in the plant extract. Preservation may comprise at least one of the following steps: anaerobic blanketing, alkalinisation (with, e.g., at least one from lime, chalk, MgO, $Mg(OH)_2$, and $MgCO_3$), acidification by addition of an organic or inorganic acid (with, e.g., at least one from lactic acid, $H_2SO_4$, and $SO_2$), acidification by inoculation (with, e.g., a lactic acid forming organism), addition of antimicrobials, irradiation (e.g. by UV- or X-rays), pasteurization (e.g. at 70-90° C. for about 20 minutes), cooling (e.g. to temperatures between 4 and 7° C.) and freezing (e.g. at temperatures below −18° C.). Sterilization may be performed, for instance, by heating (e.g. at about 120° C. for about 20 minutes) or by filtration (e.g. microfiltration).

Generally, a plant pulp or a plant juice may be used as the plant extract. Using a plant pulp as the plant extract advantageously minimizes sugar losses associated to the discard of processed plant residues. On the other hand, by using a plant juice as the plant extract the amount of solid impurities present in the extract is minimized.

When a plant pulp is used as the plant extract, the plant pulp may optionally be subjected to a treatment with pulsed electric field technology and/or to a chemical treatment (e.g. alkaline treatment) and/or to a biochemical treatment (e.g. with hydrolytic enzymes).

In a particular embodiment, the plant extract may be subjected to at least one solid/liquid separation. The solid/liquid separation may also be performed at the collecting site of plant materials. The solid/liquid separation may be performed by, for instance, centrifugation and/or filtration. The solid/liquid separation may comprise subjecting the plant extract to a heating and/or pH adjustment step to facilitate precipitation of proteins present in the extract and their removal. The separated proteins may advantageously be used as a protein source in, for instance, animal feed.

In cases wherein the salt content of the plant extract is considered to be too high, for instance when the plant extract is subjected to a concentration step, the plant extract may be subjected to a salt removal step. Salt removal may be performed, for instance, by electrodialysis, capacitive deionization or by use of ion exchange columns. The salt removal step typically involves replacing inorganic cations and/or inorganic anions by, e.g., protons and/or hydroxides respectively. Removal of sodium, potassium and calcium cations and chloride anions may be of particular interest. Without salt removal, the fermentation medium comprising such a plant extract may have a too high osmotic pressure, which is disadvantageous for growth of the microorganism and prolongs the fermentation time. A longer fermentation time is disadvantageous because the risk of contamination of the culture increases with fermentation time. In addition, a longer fermentation time reduces the efficiency of industrial processes and makes them lengthier and more costly, since more fermenter volume is required with longer fermentation times.

Prior to use, the plant extract may be stored, e.g., under cooling or freezing conditions.

In the method as described herein, the plant extract as such may be used as the fermentation medium, i.e. without any dilution or addition of other components. Alternatively, the fermentation medium may be provided by mixing the plant extract with additional nutrients and/or with water.

Depending on the concentration of fermentable carbohydrates in the plant extract, the plant extract may be diluted into the fermentation medium. The fermentation medium comprises at least 25 wt. % of the plant extract. In particular, the fermentation medium may comprise at least 50 wt. % of the plant extract, more in particular at least 75 wt. % or at least 90 wt. % or at least 95 wt. %. The percentage by weight is based on the total weight of fermentation medium before fermentation has begun, i.e. before being inoculated with the lactic acid producing microorganism.

In one embodiment the fermentation medium comprises 100 wt. % of the plant extract, i.e. the plant extract as such is used as the fermentation medium. In this embodiment, the fermentation medium comprising the plant extract is a self-sufficient fermentation medium, meaning that besides the plant extract the fermentation medium does not comprise any additional nutrients. A fermentation medium wherein the plant extract is diluted with water only is also self-sufficient.

In one embodiment, the fermentation medium comprising the plant extract may be provided with additional fermentable carbohydrates. This may be necessary if the content of fermentable carbohydrates of the plant extract is considered to be too low. It is also possible to combine a plant extract having a relatively low fermentable sugar content with a plant extract having a relatively high fermentable sugar content.

In another embodiment, the fermentation medium comprises additional nutrients besides the plant extract. The fermentation medium may be provided by mixing the additional nutrients with the plant extract and, optionally, water. The additional nutrients may be added in any order and in solid form, as solutions or as suspensions (e.g. in water).

The additional nutrients may be selected from at least one of, for instance, mineral salts (e.g. a source of mineral nitrogen, phosphate, sulfur and trace elements such as zinc, magnesium, calcium, manganese, potassium, sodium, boric, iron, cobalt, copper, molybdenum, nickel, aluminum etc.) and a source of organic nitrogen (e.g. yeast autolysates and hydrolysates, plant protein hydrolysates, animal protein hydrolysates, and soluble by-products from steeping wheat or maize). Such organic nitrogen sources generally provide nitrogen in the form of, e.g., free amino acids, oligopeptides, peptides, vitamins and traces of enzyme cofactors. Such organic nitrogen sources further may also be added individually and/or in pure form.

The pH of the fermentation medium may be adjusted to a pH suitable for fermentation with the microorganism of choice, prior to inoculation. Generally, the pH may be adjusted to a pH from about 2.0 to about 8.0, in particular from about 4.0 to about 7.5. Depending on the initial pH of the fermentation medium, adjusting the pH may be performed by addition of a base (e.g. a caustic magnesium salt) or an acid (e.g. $H_2SO_4$).

The fermentation medium is fermented by means of a lactic acid producing microorganism in the presence of a caustic magnesium salt to provide a fermentation broth containing magnesium lactate. The fermentation is generally performed by incubating the fermentation medium with the microorganism at a suitable temperature for a suitable period of time.

During fermentation, when adding a caustic magnesium salt, and when the fermentation is ended, no precipitation of magnesium lactate in whatever form should occur. Whether or not precipitation of magnesium lactate occurs will thereby depend on the concentration of fermentable carbohydrates in the fermentation medium, the fermentation temperature, the concentration of other constituents of the fermentation medium and the dilution factor of the added caustic magnesium salt. Typically, magnesium lactate remains soluble in a fermentation broth at a concentration of at the most 9.5 wt. % when measured at a temperature of 80° C.

During fermentation, carbohydrate degrading enzymes may be added to the fermentation broth to assist the degradation of fermentable carbohydrates, especially those in polymeric form. This concept of simultaneous saccharification and fermentation is described in e.g. WO 03/095659.

Suitable lactic acid producing microorganisms may include bacteria, fungi and yeasts, and may be selected from microorganisms that are (a) homolactic lactic acid producers or (b) heterofermentative microorganisms which produce lactic acid. The microorganisms may be genetically engineered to produce or overproduce lactic acid.

Examples of such microorganisms include, but are not limited to, bacterial species of the genera *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, Weissella, Bacillus* (including *Bacillus coagulans, Bacillus licheniformis, Bacillus smithii, Bacillus thermolactis* and *Bacillus thermoamylovorans*), *Geobacilus* (including *Geobacillus stearothermophilus* and *Geobacillus thermoglucosidans*), *Caldicellulosiruptor* (including *Caldicellulosiruptor saccharolyticus*), *Clostridium* (including *Clostridium thermocellum*), *Thermoanaerobacterium* (including *Thermoanaerobacterium saccharolyticum*), *Thermoanaerobacter* and *Escherichia* (including *Escherichia coli*), and fungal and yeast species from the genera *Saccharomyces* (including *Saccharomyes cerevisiae*), *Kluyveromyces* (including *Kluyveromyces lactis* and *Kluyveromyces marxianus*), *Issatchenkia* (including *Issatchenkia orientalis*), *Pichia* (including *Pichia stipitis*), *Candida* (including *Candida boidinii, Candida magnolia, Candida methanosorbosa, Candida sonorensis* and *Candida utilis*) and *Rhizopus* (including *Rhizopus arrhizus, Rhizopus microspores* and *Rhizopus oryzae*).

Bacterial genera that are of particular interest are *Lactobacillus, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*) and *Escherichia* (including *Escherichia coli*). Additionally or alternatively, preferred bacterial species are those that display optimal growth at a pH in the range of about 6 to about 8.

The incubation temperature may depend on the microorganism used. For example, the optimum temperature to be used may be established by analyzing the activity of the fermentation microorganism under different temperature conditions. Generally, the temperature may be within the range from about 20 to about 80° C., in particular within the range from about 25 to about 70° C., and more in particular within the range from about 30 to about 60° C.

The caustic magnesium salt added to the fermentation medium is used to neutralize the lactic acid excreted by the microorganisms during fermentation generating a magnesium lactate salt. A drop in pH below a critical value, depending on the microorganism used in the process, could damage the metabolic process of the microorganism and bring the fermentation process to a stop. The pH is generally adjusted during fermentation to be from about 2.0 to about 8.0, in particular from about 4.0 to about 7.5. Adjusting the pH may be performed by controlling the pH of the fermentation medium and by addition of appropriate amounts of base when necessary. The caustic magnesium salt may be selected from, for instance, at least one of MgO, $Mg(OH)_2$, $MgCO_3$ and $Mg(HCO_3)_2$. The caustic magnesium salt may contain minor amounts of other cations.

Generally, the fermentation may be stopped when the fermentation broth is substantially free of fermentable carbohydrates, e.g. when the content of fermentable carbohydrates in the liquid phase of the fermentation broth is below 5 g/l. The amount of fermentable carbohydrates may be monitored by subjecting samples of the fermentation broth to a solid/liquid separation step, to remove any solids from the liquid phase, and measuring the content of e.g. C5, C6 and/or C12 sugars in the liquid phase as described earlier for the plant extract.

Generally, the yield of lactic acid produced relative to the fermentable carbohydrates consumed (e.g. C5, C6 and/or C12 sugars) is from 70 to 100%, in particular from 80 to 100%.

The fermentation of a fermentation medium comprising a plant extract with a low content of fermentable carbohydrates in combination with caustic magnesium salt generally results in a fermentation broth comprising magnesium lactate in a concentration at which the magnesium lactate is present in solution. This allows for an improved isolation of magnesium lactate from the fermentation broth by, for instance, using a concentration step to provide magnesium lactate crystals. Having such control of the crystallization of magnesium lactate advantageously allows improving the removal of the insoluble and soluble impurities, in particular impurities originating from the low sugar plant extract.

The magnesium lactate-containing fermentation broth is subjected to a solid/liquid separation step, e.g. by flotation, sedimentation, flocculation, centrifugation, filtration, decantation, and combinations thereof, to provide a magnesium lactate-containing medium which is separated from the biomass and other solid impurities which remain in the solid residue, e.g. a filtration cake or a centrifugal cake. The solid/liquid separation is preferably performed at a temperature from 20 to 75° C., in particular from 25 to 70° C., and more in particular from 30 to 60° C. These temperatures are high enough for the magnesium lactate to remain in solution whilst maintaining some other components in the solid state. By performing the solid/liquid separation at these temperatures the separation may be improved.

Magnesium lactate crystals are generally obtained during and/or after concentration of the fermentation liquid after solid/liquid separation. Concentration may be performed by removal of water (e.g. under reduced pressure) or by means of filtration (e.g. nanofiltration). Magnesium lactate crystals may be obtained with or without cooling the concentrate. Cooling may be performed to reach temperatures below 20° C. However, it is generally preferred for the crystallization to take place a temperature from 20 to 95° C., in particular from 50 to 90° C. Crystallization at these temperatures (e.g. without cooling) advantageously allows a higher amount of other impurities, in particular salts originating from the low-sugar plant extract, to remain in the liquid phase, thereby avoiding their co-precipitation or co-crystallization with the magnesium lactate crystals.

It has been found that the use of caustic magnesium salt during fermentation allows such a selective crystallization of the magnesium lactate product leaving behind the relatively high amount of impurities originating from the low-sugar plant extract as well as any impurities derived from the fermentation. These impurities may be converted, e.g. after separation from the magnesium-lactate crystals, into a fertilizer or used directly as a fertilizer. Conversion of the impurities into a fertilizer may comprise at least one processing step selected from an evaporation, a concentration, a chemical reaction (e.g. with phosphates, ammonia and/or potassium salts), a precipitation and a solid/liquid separation. Examples of fertilizers that may be obtained include fertilizers rich in magnesium (e.g. struvite).

The magnesium lactate crystals may then be separated by solid/liquid separation and washed.

The concentration of magnesium lactate in the liquid phase of the concentrated medium or the concentrated broth may depend on the temperature and the amount of other components in the liquid phase. The concentration of magnesium lactate may generally be from 7 to 15 wt. % based on the total weight of the liquid phase, in particular from 7.5 to 10 wt. %.

Generally, the yield of recovery of lactic acid in the form of magnesium lactate crystals may be from 50% to 99%, in particular from 70% to 99% based on the amount of lactic acid produced during fermentation.

The magnesium lactate crystals may be subjected to a step to convert the magnesium lactate salt (first lactate salt) to a different lactate salt (second lactate salt). For instance, the magnesium lactate may be subjected to a salt exchange reaction with a monovalent base (e.g. a hydroxide of sodium, potassium, calcium, and/or ammonium) to form a monovalent lactate salt and magnesium hydroxide. See also WO 2005/123647, which is incorporated herein by reference and which describes the production of lactic acid and/or lactate from a magnesium lactate comprising medium by a salt exchange reaction between magnesium lactate and a monovalent base. In particular, as described in WO 2005/123647, the magnesium lactate may be reacted with the monovalent base at a pH range between 9 and 12, preferably between 9.5 and 11 to form the monovalent lactate salt and magnesium hydroxide.

When the method as described herein is used for preparing lactic acid, the magnesium lactate or the second lactate salt may be converted to lactic acid by an ion exchange method, e.g. by use of an ion exchange column or electrodialysis. The magnesium lactate or second lactate salt may also be acidified with a strong acid (e.g. sulfuric acid, HCl and $HNO_3$) to provide a mixture of lactic acid and a magnesium salt. This mixture is subsequently subjected to a lactic acid/magnesium salt separation step and/or to a magnesium salt splitting step. Reference is made to WO 2011/095631, which contents incorporated herein by reference and which describes a process for the preparation of lactic acid. This process comprises subjecting a magnesium lactate to a salt exchange reaction to provide a monovalent lactate salt, and subjecting the monovalent lactate salt to water-splitting electrodialysis, to produce lactic acid. In particular, as described in WO 2011/095631, the water-splitting electrodialysis may be performed on an aqueous medium wherein the concentration of the monovalent lactate salt is of a value between 10 and 30 wt. %, and the electrodialysis may be carried out to a partial conversion of 40 to 98 mole % to produce a first solution comprising monovalent base and a second solution comprising lactic acid and monovalent lactate salt. The second solution comprising lactic acid and monovalent lactate salt may then be separated into lactic acid and a solution comprising the monovalent lactate salt by vapour-liquid separation. The solution comprising the monovalent lactate salt may be recycled for addition to the monovalent lactate salt solution to, e.g., adjust the concentration of monovalent lactate salt to the desired level.

Recovering the lactate or lactic acid from the magnesium lactate-containing fermentation broth may further comprise, for instance, at least one of liquid/liquid extraction, nanofiltration, active carbon treatment, distillation and re-crystallization. These treatments may be used to further remove impurities from the lactate or lactic acid products.

The present invention is further illustrated by the following Examples, without being limited thereto or thereby.

EXAMPLES

Determination of Magnesium Lactate

Magnesium lactate may be determined by using any method known to the person skilled in the art. It is convenient to determine magnesium and lactate separately. Magnesium determination is done by atomic absorption spectrometry (Varian spectrAA 220 FS) and lactate determination is done by gas chromatography (Thermo Scientific Trace GC Ultra) of the corresponding methyl ester. The methods are validated by the use of appropriate standards.

Characterization of Paper Sludge Hydrolysate

A plant extract was obtained by hydrolyzing paper sludge with cellulolytic enzymes. Suspended particles were removed from the hydrolysate.

Part of the hydrolysate was treated with a ion exchange column to reduce the level of ions. This is evidenced by the reduced amount of sodium, potassium and calcium cations present in the hydrolysate subjected to the ion exchange treatment (PSH with IEX) when compared to the hydrolysate which has not been subjected to the ion exchange treatment (PSH without IEX).

The composition of the paper sludge hydrolysate is shown in Table 1.

Hydrolysates with glucose concentrations higher than 9 wt. % were obtained by concentrating (by water removal) the hydrolysate having an initial concentration of 9 wt. % of glucose (with and without ion exchange treatment). Thereby hydrolysates with a glucose concentrations of 14 wt. %, 16 wt. %, 18 wt. % and 20 wt. % respectively were obtained. The composition of the hydrolysates with these different glucose concentration is also indicated in Table 1.

TABLE 1

Composition of the Paper Sludge Hydrolysate (PSH) with and without ion exchange (IEX) treatment.

| Glucose | Inorganics (Ca, Na and K) (mg/kg) | |
|---|---|---|
| (wt. %) | Without IEX | With IEX |
| 9 | 2884 | 22 |
| 14 | 4486 | — |
| 16 | 5128 | 39 |
| 18 | 5769 | 44 |
| 20 | 6410 | 49 |

The ion exchange treatment was performed using a column containing Amberlite FPA53 or Amberlite IR120H resins.

The amount of sugars was determined by high-pH anion exchange chromatography coupled with a pulsed amperometric detection (HPAEC-PAD). The amount of sodium, potassium and calcium cations was determined by AAS (atomic absorption spectrometry) (Varian spectrAA 220 FS).

Production of Magnesium Lactate Crystals

The paper sludge hydrolysate with a glucose concentration of 9 wt. % and subjected to ion exchange treatment was fermented with lactic acid producing bacteria largely composed of B. coagulans.

Prior to fermentation, the PSH was supplied with typical medium nutrients: ammonium salts, methionine, biotin, thiamine, calcium salts, potassium salts, and salts of trace elements to provide the fermentation medium. The medium was then inoculated with the lactic acid producing bacteria.

The fermentation was performed at 50-55° C. and at a pH of 6.5-7.0, which was kept constant by neutralization with $Mg(OH)_2$.

After ending the fermentation, the resulting broth was cleared from suspended solids (including the biomass) by centrifugation at a temperature between room temperature and fermentation temperature. The clear fermentation broth was subjected to evaporative crystallization (under vacuum at 70° C.), whereby water was continuously removed from the cleared fermentation broth. Crystals of magnesium lactate dihydrate were formed during the evaporative crystallization at 70° C. The resulting suspension of crystals in the mother liquor was separated by filtration. The crystals were washed with water.

The yield of recovery of magnesium lactate in the form of crystals was of 86% (calculated on the basis of the weight amount of magnesium lactate present in the broth after fermentation and biomass separation). The magnesium lactate crystals obtained had a lactate stereochemical purity of 99.9% and a magnesium lactate dihydrate content (on dry solid basis) of 92 wt. %.

This example shows that magnesium lactate crystals of high quality can be obtained with high recovery yield when starting from a paper sludge hydrolysate with a glucose content of 9 wt. % by using magnesium hydroxide as the neutralizing agent.

This is achieved without adding additional fermentable carbohydrate sources to the paper sludge hydrolysate and without having to concentrate the initial paper sludge hydrolysate in order to start from higher sugar concentrations.

Fermentation Time

Paper sludge hydrolysates (PSH) with different concentrations of glucose with and without ion exchange treatment (see table 1 and 2) and "control" aqueous solutions of glucose with different glucose concentrations (see table 2) were fermented as described above for the PSH with a 9 wt. % glucose content (Table 2).

The control aqueous glucose solution was prepared by diluting glucose in water.

The fermentation was considered to be ended when the base consumption was dropped to zero or nearly zero. Confirmation was done by analyzing sugar levels (determined as described above for the hydrolysate). The results are shown in Table 2.

Longer fermentation times indicate that the fermentation takes a longer time to reach completion, which is undesired, as indicated hereinabove.

TABLE 2

Fermentation of Paper Sludge Hydrolysate (PSH) with and without ion exchange (IEX) treatment and of control aqueous glucose solutions.

| Initial | Fermentation Time (h) | | |
|---|---|---|---|
| glucose (wt. %) | PSH (without IEX) | PSH (with IEX) | Control |
| 9 | 11 | 11 | nd |
| 14 | 22 | nd | 13 |
| 16 | 27 | 20 | 14 |
| 18 | 30 | 25 | nd |
| 20 | 50 | 30 | nd |

As can be seen in Table 2 the fermentation time increases with the initial concentration of glucose. The increase of fermentation time is much less pronounced when using an aqueous glucose solution (control) or a paper sludge hydrolysate subjected to an ion exchange treatment (PSH with IEX).

When comparing a paper sludge hydrolysate with or without ion exchange treatment (PSH with or without IEX) it can be seen that an ion exchange treatment significantly reduces the fermentation time. This is particularly so when starting from paper sludge hydrolysates having glucose concentrations higher than 9 wt. %. This reduction is more pronounced when comparing the paper sludge hydrolysate without ion exchange treatment and the control solution. For instance, for the experiments performed with a starting glucose concentration of 16 wt. % the fermentation time is reduced from 27 h to 20 h when the PSH is subjected to a ion exchange treatment, and to 14 h when an aqueous glucose solution is used (control). This is even more pronounced for paper sludge hydrolysates with a starting concentration of 20 wt. % of glucose, which fermentation time is reduced from 50 h to 30 h when the PSH is subjected to an ion exchange treatment.

In contrast, when the initial glucose concentration is kept low (i.e. 9 wt. % of glucose) the fermentation time remains the same (i.e. 11 h), irrespective of whether the glucose source is a paper sludge hydrolysate which is not subjected to ion exchange (PSH without IEX), a paper sludge hydrolysate which is subjected to ion exchange (PSH with IEX), or an aqueous solution of glucose (control).

This shows that when starting with a plant extract with low glucose concentration the fermentation time is advantageously kept low without requiring expensive ion exchange treatments. Further, the use of a caustic magnesium salt for neutralization allows recovery of magnesium lactate of high quality and high recovery yield despite the low concentration of glucose. This shows that the method used precludes the need for using additional expensive carbohydrate sources and to concentrate the initial plant extract which, as shown, results in increased fermentation times.

The invention claimed is:

1. A method for producing lactate or lactic acid from a plant extract via fermentation comprising
   a. providing a fermentation medium comprising at least 25 wt. % of a plant extract containing fermentable carbohydrates;
   b. fermenting the fermentation medium by means of a lactic acid producing microorganism in the presence of a caustic magnesium salt to provide a fermentation broth containing at the most 9.5 wt. % magnesium lactate at the end of fermentation, the magnesium lactate being in soluble form during and at the end of fermentation; and
   c. recovering lactate or lactic acid from the magnesium lactate containing fermentation broth,
   wherein the plant extract contains fermentable carbohydrates in a concentration of 0.5-9.5 wt. %.

2. The method according to claim 1 wherein the fermentation medium contains fermentable carbohydrates in a concentration of at most 9.5 wt. %.

3. The method according to claim 1 wherein the plant extract is an extract of oil palm fronds.

4. The method according to claim 1 wherein the caustic magnesium salt is selected from at least one of MgO, $Mg(OH)_2$, $MgCO_3$ and $Mg(HCO_3)_2$.

5. The method according to claim 1 wherein the fermentation medium contains additional fermentable carbohydrates besides the fermentable carbohydrates provided by the plant extract.

6. The method according to claim 1 wherein the fermentation medium contains at least one additional nutrient besides the nutrients provided by the plant extract.

7. The method according to claim 1, wherein the plant extract is the only source of fermentable carbohydrates.

8. The method according to claim 1 wherein recovering lactate or lactic acid comprises i) subjecting the fermentation broth containing magnesium lactate to a solid/liquid separation to provide a medium comprising magnesium lactate in solution and a solid residue; ii) concentrating the medium comprising magnesium lactate to provide a concentrated medium comprising magnesium lactate crystals; and iii) subjecting the concentrated medium comprising magnesium lactate crystals to a solid/liquid separation to provide magnesium lactate crystals.

9. The method according to claim 8 wherein the magnesium lactate crystals are obtained during and/or after concentration at a temperature from 20 to 95° C.

10. The method according to claim 8 wherein the magnesium lactate crystals are obtained during and/or after concentration at a temperature from 50 to 90° C.

11. The method according to claim 8 wherein the solid/liquid separation of step i) is performed at a temperature from 20 to 75° C.

12. The method according to claim 8 wherein the solid/liquid separation of step i) is performed at a temperature from 30 to 60° C.

13. The method according to claim 1 wherein the plant extract contains fermentable carbohydrates in a concentration of 2-9.5 wt. %.

14. The method according to claim 1 wherein the plant extract contains fermentable carbohydrates in a concentration of 3-9.5 wt. %.

15. The method according to claim 1 wherein the plant extract contains fermentable carbohydrates in a concentration of 1-8 wt. %.

16. The method according to claim 1 wherein the plant extract contains fermentable carbohydrates in a concentration of 2-5 wt. %.

17. The method according to claim 1 wherein the fermentation medium comprises at least 90 wt. % of the plant extract containing fermentable carbohydrates, based on the total weight of fermentation medium before inoculation with the lactic acid producing microorganism.

18. The method according to claim 1 wherein the fermentation medium comprises at least 95 wt. % of the plant extract containing fermentable carbohydrates, based on the total weight of fermentation medium before inoculation with the lactic acid producing microorganism.

19. The method according to claim 1 wherein the fermentation medium comprises 100 wt. % of the plant extract containing fermentable carbohydrates, based on the total weight of fermentation medium before inoculation with the lactic acid producing microorganism.

20. A method for producing lactate or lactic acid from a plant extract via fermentation comprising
   a. providing a fermentation medium comprising at least 25 wt. % of a plant extract containing fermentable carbohydrates;
   b. fermenting the fermentation medium by means of a lactic acid producing microorganism in the presence of a caustic magnesium salt to provide a fermentation broth containing at the most 9.5 wt. % magnesium lactate at the end of fermentation, the magnesium lactate being in soluble form during and at the end of fermentation; and c. recovering lactate or lactic acid from the magnesium lactate containing fermentation broth, wherein the plant extract is an extract of oil palm fronds, and wherein the plant extract has a liquid phase and said liquid phase contains fermentable carbohydrates in a concentration of 0.5-9.5 wt. %.

21. The method according to claim 1 wherein the plant extract comprises paper sludge hydrolysate.

* * * * *